(12) United States Patent
Tong et al.

(10) Patent No.: US 7,162,305 B2
(45) Date of Patent: Jan. 9, 2007

(54) FUNCTIONAL ELECTRICAL STIMULATION SYSTEM

(75) Inventors: Kai-Yu Tong, Hong Kong (HK); Arthur F. T. Mak, Hong Kong (HK); Kelvin T. Y. Leung, Hong Kong (HK)

(73) Assignee: The Hong Kong Polytechnic University, Hong Kong (HK)

( * ) Notice: Subject to any disclaimer, the term of this patent is extended or adjusted under 35 U.S.C. 154(b) by 440 days.

(21) Appl. No.: 10/278,575

(22) Filed: Oct. 23, 2002

(65) Prior Publication Data

US 2004/0082979 A1    Apr. 29, 2004

(51) Int. Cl.
*A61N 1/36* (2006.01)

(52) U.S. Cl. .......................................... 607/48

(58) Field of Classification Search ................. 607/48, 607/62, 49, 46, 50, 52; 600/595
See application file for complete search history.

(56) References Cited

U.S. PATENT DOCUMENTS

| | | | | |
|---|---|---|---|---|
| 3,911,910 A | * | 10/1975 | Oesau | 602/2 |
| 4,558,704 A | * | 12/1985 | Petrofsky | 607/48 |
| 4,580,569 A | * | 4/1986 | Petrofsky | 607/48 |
| 4,917,093 A | * | 4/1990 | Dufresne et al. | 607/62 |
| 5,330,516 A | * | 7/1994 | Nathan | 607/48 |
| 5,358,471 A | * | 10/1994 | Klotz | 602/21 |
| 5,540,735 A | * | 7/1996 | Wingrove | 607/46 |
| 5,548,735 A | | 8/1996 | Chen et al. | |
| 5,562,707 A | * | 10/1996 | Prochazka et al. | 607/2 |
| 5,643,332 A | * | 7/1997 | Stein | 607/49 |
| 5,748,845 A | | 5/1998 | Labun et al. | |
| 5,769,875 A | | 6/1998 | Peckham et al. | |
| 5,974,342 A | | 10/1999 | Petrofsky | |
| 5,980,472 A | * | 11/1999 | Seyl | 600/587 |
| 6,026,328 A | * | 2/2000 | Peckham et al. | 607/48 |
| 6,042,555 A | * | 3/2000 | Kramer et al. | 600/595 |
| 2001/0000187 A1 | * | 4/2001 | Peckham et al. | 607/48 |

\* cited by examiner

*Primary Examiner*—George R. Evanisko
*Assistant Examiner*—Michael Kahelin
(74) *Attorney, Agent, or Firm*—Jackson Walker, LLP

(57) ABSTRACT

An electrical stimulation device for a body part of a person comprises an orthotic with sensor and electrodes and a controller. The controller receives a sensor signal, compares the sensor signal to a threshold value and generates an electrical output from the electrodes if the sensor signal exceeds the threshold value. A docking station facilitates connection of the electrodes and sensors to a computer. The docking station including a first processor for measuring values of the sensor signal and the electrical outputs and a second processor for generating electrical outputs on the electrodes.

6 Claims, 6 Drawing Sheets

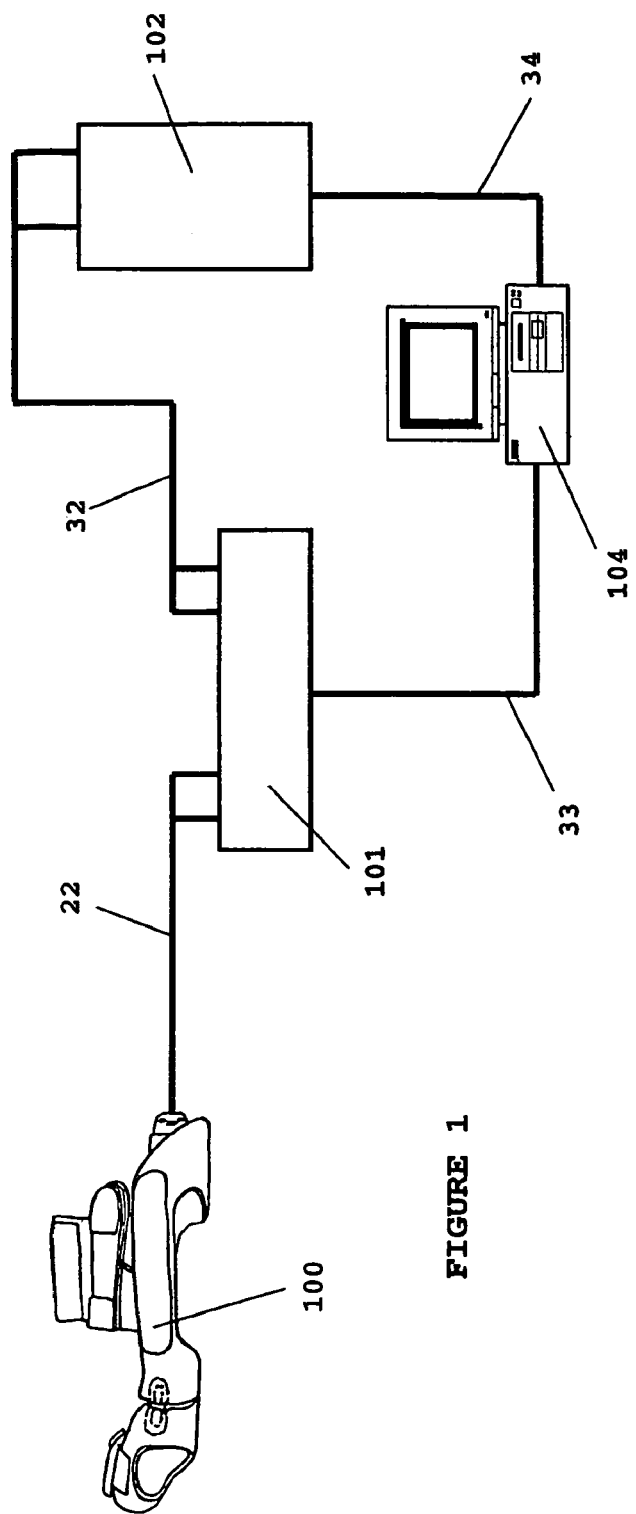
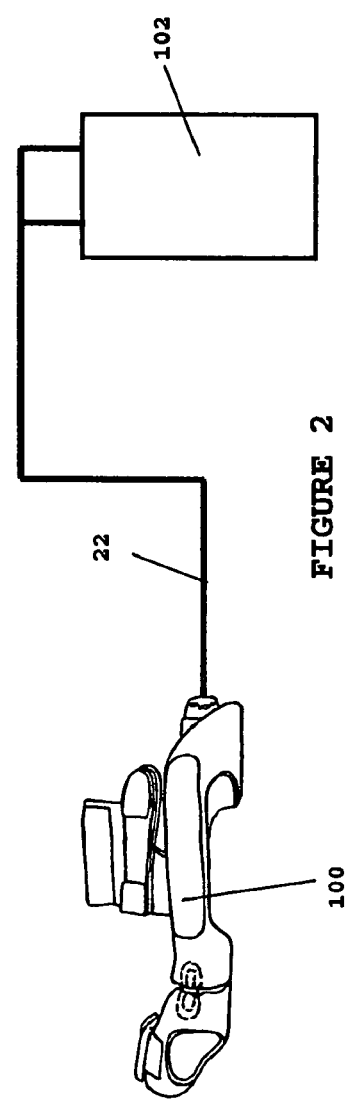
FIGURE 1
FIGURE 2

FUNCTIONAL ELECTRICAL STIMULATION SYSTEM

BACKGROUND OF THE INVENTION

1. Field of the Invention

The present invention relates to Functional Electrical Stimulation Systems.

2. Background Information

Functional Electrical Stimulation (FES) systems artificially stimulate the muscles, and muscle groups, of persons through the use of electrical current in order to stimulate movement. As early as 1971 Liberson applied electrical stimulation to assist walking in patients with foot drop. Current FES systems are mainly designed for persons after a spinal cord injury and stroke.

Several different groups of researchers have designed implant electrodes and systems for spinal cord injured persons. These systems need to be surgically implanted into muscle groups and are aimed at control of deep muscles.

After stroke patients often suffer from weakness in the extensor muscle on the upper limb and involuntary muscular contractions due to spasticity of the flexor muscle groups. FES can be used with stroke victims to stimulate the extensor muscle to open the hand and reduce the spasticity. FES can be used for therapeutic training and some patients have been found to partially or completely recover hand functions. Therefore. it is not necessary to have the implant system.

SUMMARY OF THE INVENTION

It is an object of the present invention to provide a Functional Electrical Stimulation systems which assists with rehabilitation of stroke patients, or which at least offers a useful choice.

According to a first aspect of the invention there is provided an electrical stimulation device comprising:
  an orthotic for a body part of a person,
  a sensor on the orthotic for detecting movement of the body part,
  an electrode on the orthotic for contacting the skin surface over a muscle of the body part, and
  a controller in electrical communication with the sensor and electrode for receiving a sensor signal, comparing the sensor signal to a threshold value and generating an electrical output from the electrode if the sensor signal exceeds the threshold value.

According to a second aspect of the invention there is provided an electrical stimulation device comprising:
  an orthotic for a body part of a person,
  a first sensor on the orthotic for detecting a first movement of the body part
  a second sensor on the orthotic for detecting a second movement of the body part,
  a plurality of electrodes on the orthotic for contacting the skin surface over muscles of the body part, and
  a controller in electrical communication with the sensors and electrodes for receiving a first sensor signal and comparing it to a first threshold value, receiving a second sensor signal and comparing it to a second threshold value, and generating an electrical output from a first group of electrodes if the first sensor signal exceeds the first threshold value, or generating the electrical output from a second group of electrodes if the first sensor signal exceeds the first threshold value and the second sensor signal exceeds the second threshold value.

Preferably, the body part is an upper limb, the first movement is extension of the wrist, the second movement is rotation of the wrist, and the muscles are thumb abductor, thenar, wrist extensor, and wrist flexor muscles.

Preferably, the first sensor is an accelerometer and the first movement is extension of the wrist, and second sensor is a gyroscope and the second movement is rotation of the wrist.

Preferably, the orthotic includes a first elongate member for locating on a anterior portion of a forearm of the person, a dorsal strap extending across a posterior portion of the forearm, a second elongate member disposed on the dorsal strap of locating against the posterior portion of the forearm, and a hand member for locating about a wrist and palm of the person, the wrist member being flexibly engaged with the first elongate member for allowing movement of the wrist.

Preferably, the device includes a docking station for connecting the electrodes and sensors to a computer, the docking station including a first processor for measuring values of the sensor signals and the electrical output and communicating said values to the computer, and a second processor for generating electrical outputs on the electrodes in response to communications from the computer.

Preferably, the controller is connectable to the computer for uploading parameters including the first and second threshold values from the computer to the controller.

Preferably, the first group of electrodes are located on the skin surface over the thumb abductor and wrist extensor muscles, and the second group of electrodes are located on the skin surface over the Thenar and wrist extensor muscles.

According to a third aspect of the invention there is provided a method of controlling movement of a body part of a person including the steps of:
  detecting a movement of a body part,
  generating a signal proportional to the movement,
  comparing the signal to a threshold value, and
  delivering an electric current to a muscle in the body part for a predetermined time if the signal exceeds the threshold value.

Preferably, the method includes an intermediate step of:
  detecting a second movement of the body part,
  generating a second signal proportional to the second movement,
  comparing the second signal to a second threshold value, and wherein
  the electric current is delivered to a second muscle in the body part if the signal exceeds the threshold value and the second signal exceeds the second threshold value.

Further aspects of the invention will become apparent from the following description, which is given by way of example only.

BRIEF DESCRIPTION OF THE DRAWINGS

Embodiments of the invention will now be described with reference to the accompanying drawings in which:

FIG. 1 is a schematic of a first configuration of a Functional Electrical Stimulation (FES) system according to the invention, FIG. 2 is a schematic of a second configuration of the Functional Electrical Stimulation (FES) system.

DESCRIPTION OF THE PREFERRED EMBODIMENTS

Figure 3:
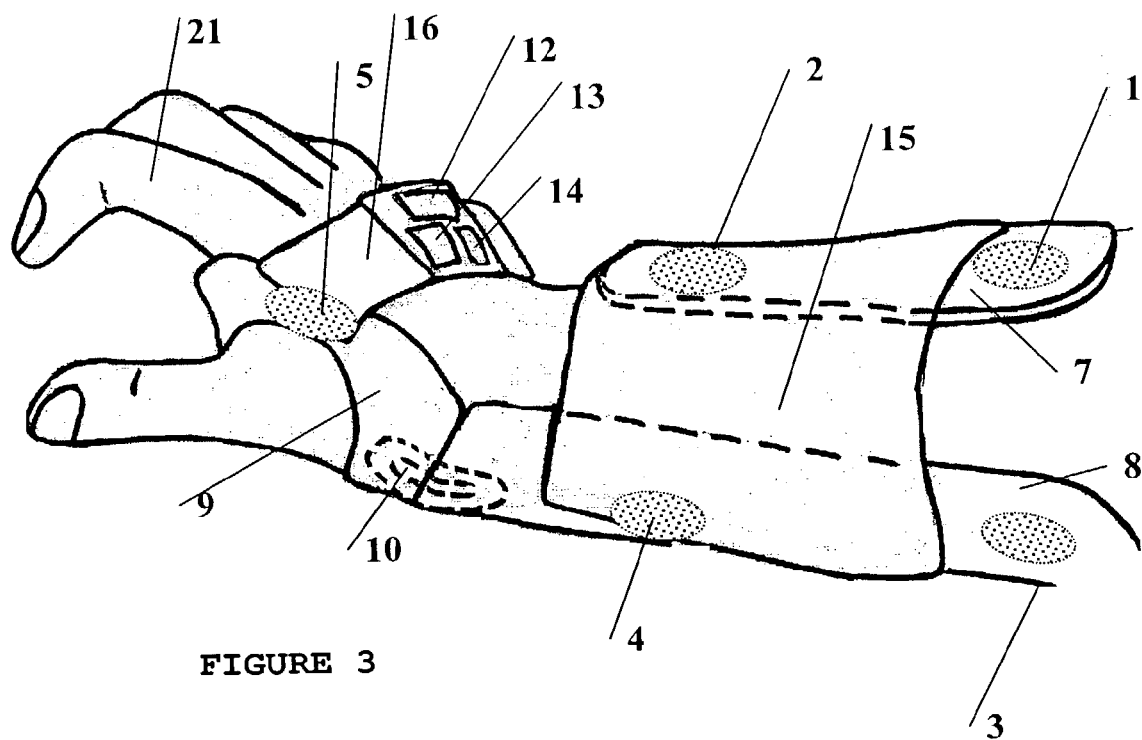
FIG. 3 is a perspective view of an Orthosis of the FES system.
Figure 4:
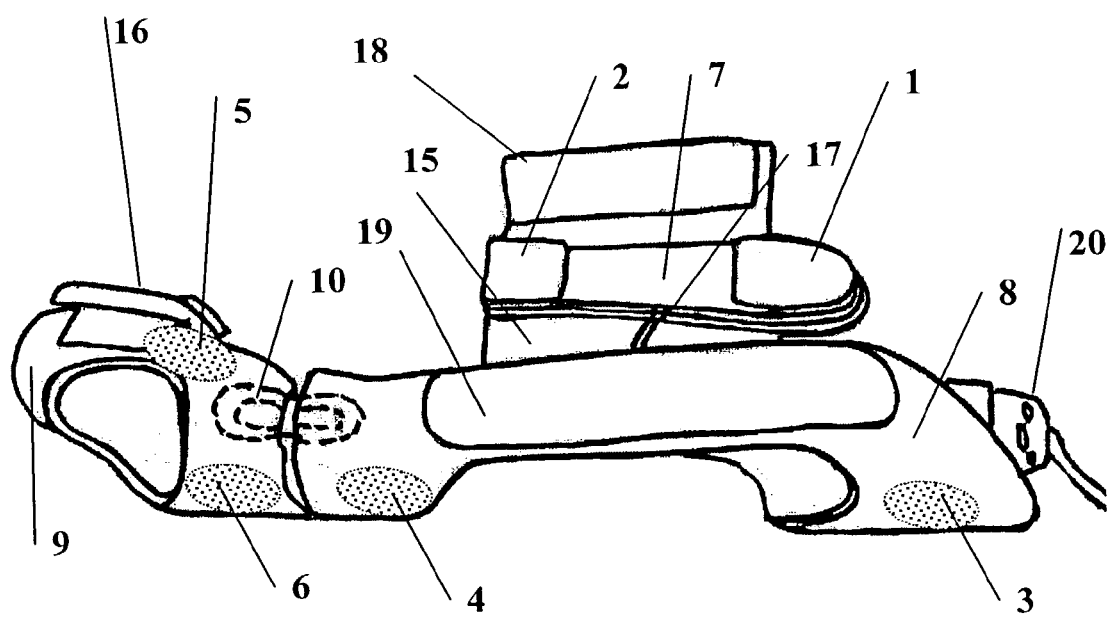
FIG. 4 is a side view of the orthosis.
Figure 5:
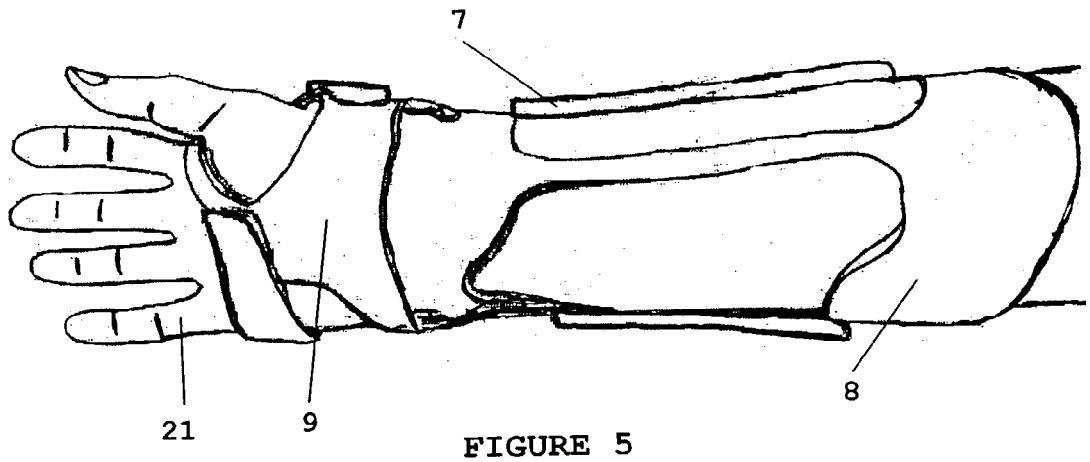
FIG. 5 is a bottom view of the orthosis.
Figure 6:
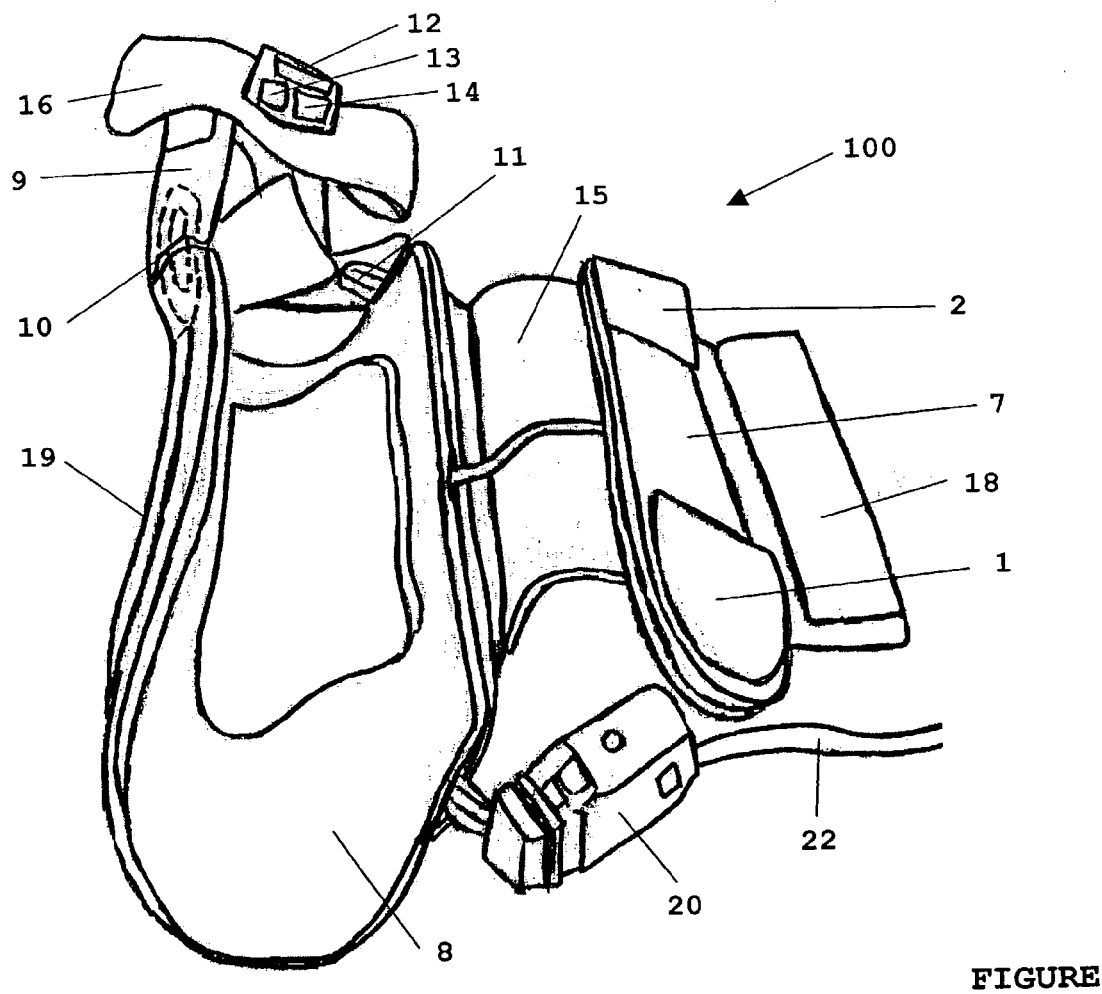
FIG. 6 is a second perspective view of the orthosis.

FIGS. 1 and 2 are schematics of a Functional Electrical Stimulation (FES) system. It consists of three basic parts: a hand-wrist orthosis 100, a portable stimulation unit 102 and a docking station 101. The FES interfaces with a computer 104. The functional electrical stimulation system has two basic configurations. FIG. 1 illustrates the first configuration, which is for training and parameter setup. FIG. 2 illustrates the second configuration in which the portable stimulation unit works in standalone mode without connection to the docking station. These configurations will be described in more detail later.

Referring to FIGS. 3 to 6, the hand-wrist orthosis 100 is made of plastic material moulded to fit the shape of the forearm of a stroke affected hand 21 of a patient. The orthosis 100 comprises three pieces. These are: a posterior portion 7, anterior portion 8, and a hand portion 9. The hand portion 9 is connected with the anterior portion 8 by two joints 10, 11 on the lateral sides. The joints 10, 11 allow flexibility for wrist movement. A strap 15 is attached to one side of the anterior portion 8 and passes over the top part of the patients forearm to detachably connect with the other side of the anterior portion 8 by Velcro™ fasteners 18, 19. The posterior aspect 7 is mounted on the strap 15 for location on the top part of the patients forearm.

The hand portion 9 includes two electrodes 5, 6. A thenar electrode 5 is for stimulating the thenar muscle group and a thumb electrode 6 is for stimulating the thumb abductor. The posterior portion 7 includes two electrodes 1, 2 for stimulating the wrist extensor muscle group. The anterior portion 8 includes two electrodes 3 and 4 for stimulating the wrist flexor muscle group. The electrodes 1, 2, 3, 4, 5, 6 are self-adhesive type electrodes located on the inner surface of the orthosis 100 to correspond to the above mentioned muscle groups. The electrodes are located by a clinician to suit the patient.

For stimulating the thenar group electrode 5 is the Active pole and electrode 4 is the Indifferent pole. For stimulating the Thumb abductor electrode 6 is the Active pole and electrode 4 is the Indifferent pole. For stimulating the Wrist extensor electrode 1 is the Active pole and electrode 2 is the Indifferent pole. And for stimulating the Wrist flexor electrode 3 is the Active pole and electrode 4 is the Indifferent pole. An Active pole is the negative terminal and an Indifferent pole is the positive terminal.

A pressure sensor 12, accelerometer 13 and gyroscope 14 are located on a strap 16 on the back of hand portion 9. The sensors provide feedback of hand movement and position.

Signal wires from sensors and electrodes on the orthosis 100 are brought together at a connector 20 on the anterior portion 8. The orthosis 100 is linked to the portable stimulation unit 102 or docking station 101 by signal cable 22.

Figure 7:
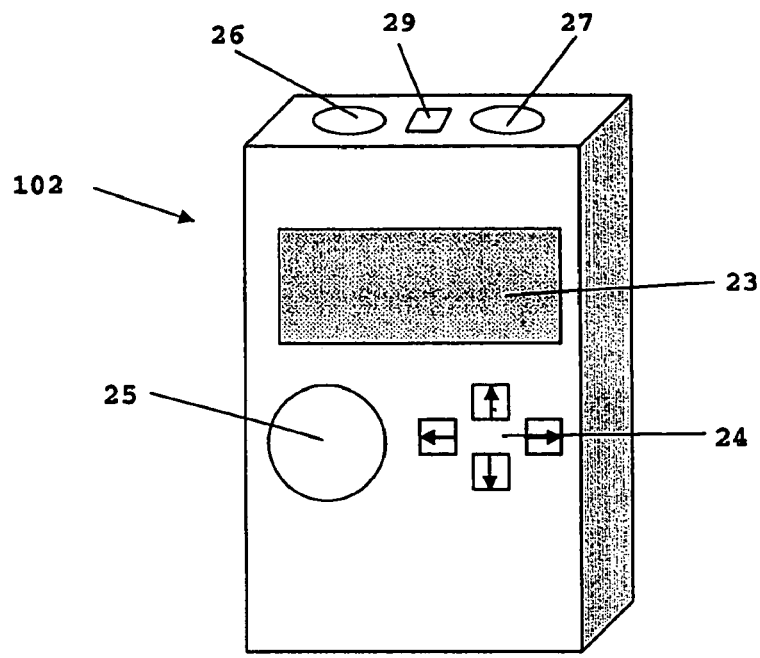
FIG. 7 is an illustration of a Portable Stimulation Unit for the FES system.
Figure 8:
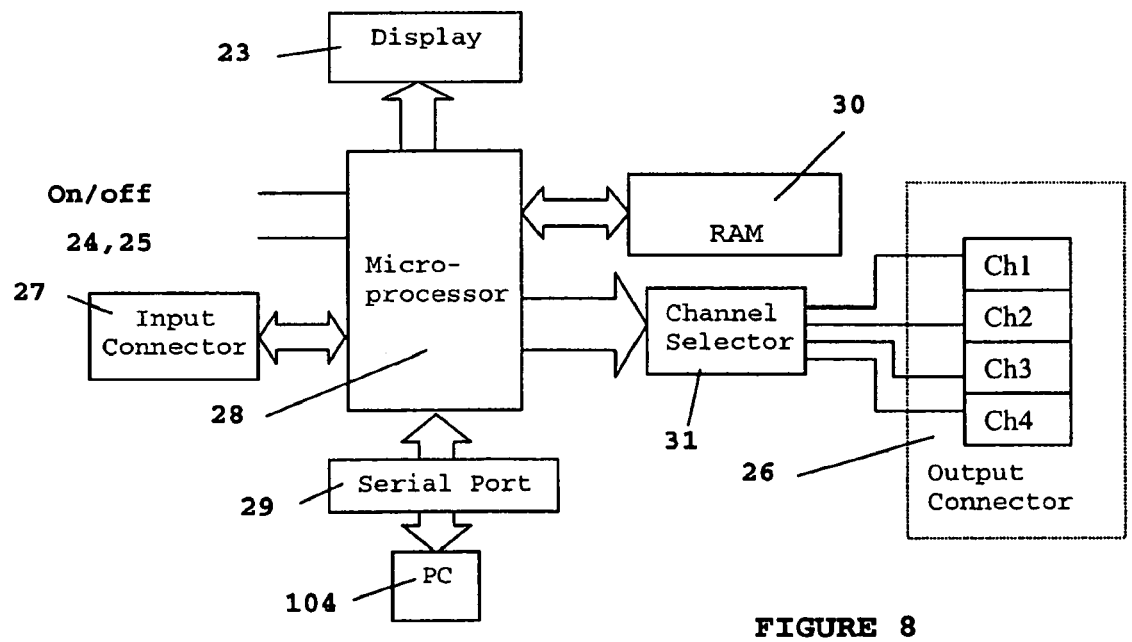
FIG. 8 is a schematic view of the control system for the Portable Stimulation Unit.

Referring to FIGS. 7 and 8, the portable stimulation unit 102 generates a train of electrical pulse, which it transmits to selected electrodes to stimulate selected muscles and coordinate muscle contractions. The portable stimulation unit 102 is controlled by a microprocessor 28. Stimulation parameters are stored in Random Access Memory (RAM) 30. An output channel selector 31 and electrode output connector 26 transmit the train of electrical pulse to the electrodes. Feedback from the sensors is input to the microprocessor 28 via input connector 27.

Manual control of the portable stimulation unit 102 is provided by a user interface means comprising a 12×2 Liquid Crystal Display 23, up/down/left/right input buttons 24 and a selection input button 25 on a front panel of the portable stimulation unit 102. The LCD display 25 provides information about the stimulation patterns and the user can adjust parameters such as the stimulation frequency, stimulation amplitude levels, sensor-threshold values, pulse widths, duration time using the interface means.

The portable stimulation unit B can interface with the computer 104 via a serial port 29 to facilitate download of simulation parameters obtained during setup and training.

The docking station 101 comprises two microprocessors and input and output connectors for the sensors and electrodes. Both the input and output connectors are connected to an input microprocessor for capture of real-time signals from the sensors and feedback of electrode output signal parameters. The output connector is connected to an output microprocessor for output of electrode control signals. The docking station 101 also includes a parallel connector for interface to the host computer 104 that facilitates graphical displays showing input and output signal parameters, parameter adjustment and data logging.

The functional electrical stimulation system has two basic configurations. A first configuration is for training and parameter setup. In this first configuration the connector lead 22 from sensor and electrodes on the orthosis 100 are connected to the input/output connectors of the docking station 101, and an extension cable 32 from the docking station 101 connect to the portable simulation unit 102. The docking station 101 also includes a parallel connector 33 for interface to the host computer 104 that facilitates graphical displays showing input and output signal parameters, parameter adjustment and data logging. At the end of the training and parameter setup session the simulation parameters are uploaded from the computer 104 to the Portable Simulation Unit 102 via a serial connection 34.

In a second configuration the orthosis 100 and portable stimulation unit 102 work in standalone mode without connection to the docking station 101 or computer 104. In this second configuration the input/output cables 22 from the orthosis 100 connect directly to the portable stimulation unit 102. This allows the patient to go home, or go about there daily routine, without the need to carry/wear bulky equipment. The portable simulation unit 102 responds to input signals to generate output signals according to the simulation parameters uploaded from the computer 104. Minor adjustment of simulation parameters and control of the portable simulation unit 102 are achieved via the user interface means.

Figure 9:
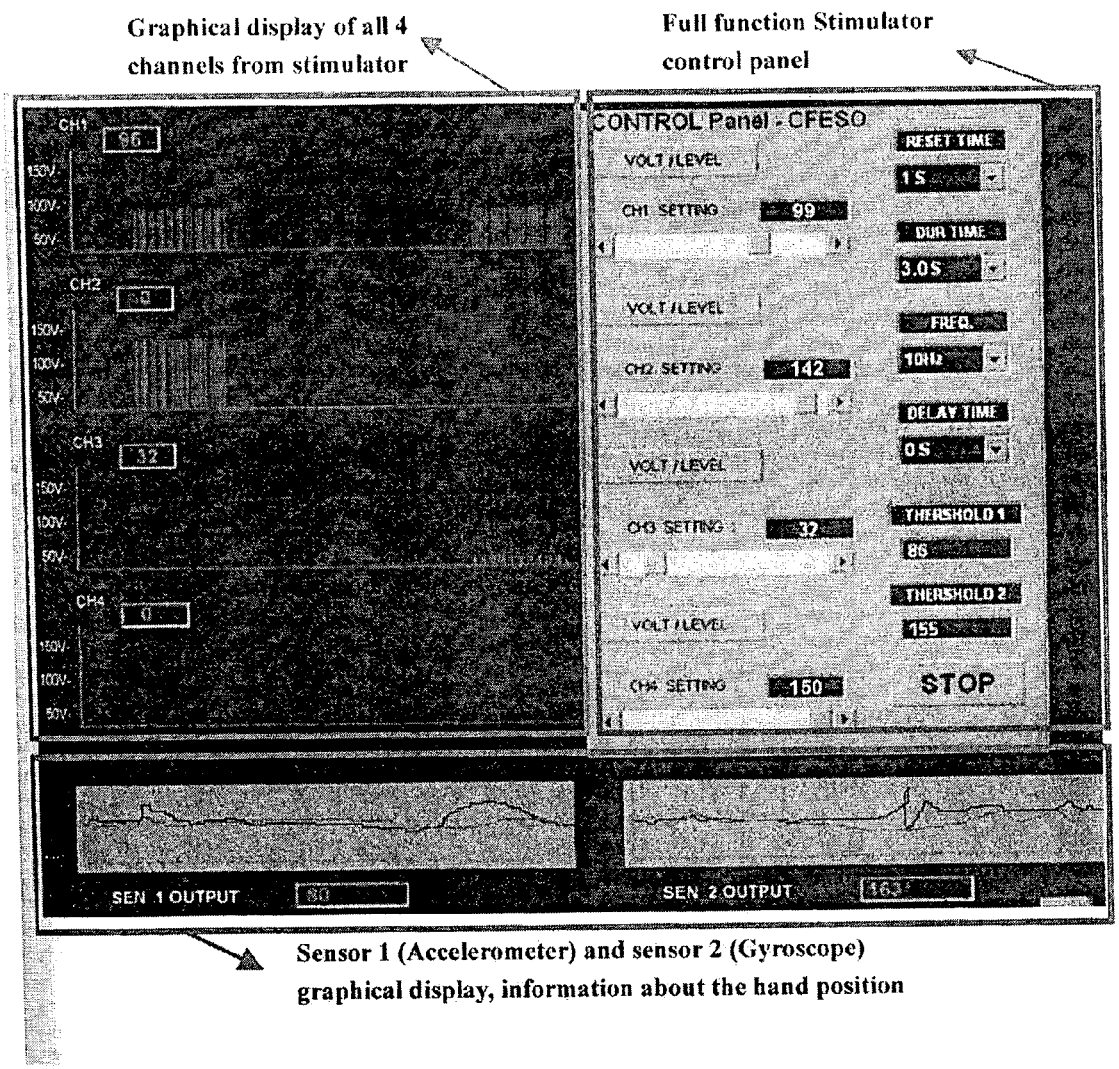
FIG. 9 is an illustration of a computer graphical user interface for use with the FES system.

Referring to FIG. 9, a layout of a Graphical User Interface on a computer is shown. A Microsoft Windows® based Graphical User Interface can be programmed in Visual Basic® or constructed using an application such as Lab View® available from National Instruments® (www.ni-.com).

The simulation parameters and their respective range are set out in the following table.

| | |
|---|---|
| Input 1 Threshold 1 | 256 levels; 0 to 5 Volts |
| Input 2 Threshold 2 | 256 levels; 0 to 5 Volts |
| Output Channel 1 Amplitude | 256 levels; 0 to 100 mA |
| Output Channel 2 Amplitude | 256 levels; 0 to 100 mA |
| Output Channel 3 Amplitude | 256 levels; 0 to 100 mA |
| Output Channel 4 Amplitude | 256 levels; 0 to 100 mA |
| Output Frequency | 10 Hz, 20 Hz, 30 Hz, 40 Hz, or 50 Hz |
| Output Pulse Width | 256 levels: 0–500 µs |
| Reset Time | 0 to 9 Seconds |
| Output Delay time | 0 to 4.5 Seconds |
| Output Duration Time | 0 to 99 Seconds |

The microprocessor may set the output on each channel to one of 256 levels within a range of 1 to 100 mA. The required level for each channel, to achieve the required muscle group stimulation, is determined during the setup mode (configuration 1) where monitoring feedback of the output parameters is possible. This level is stored in the portable stimulation unit for recall during standalone use.

The muscle groups stimulated by each channel are:

| | |
|---|---|
| Channel 1: | Electrode 6 and 4 for stimulating the thumb abductor. |
| Channel 2: | Electrode 5 and 4 for stimulating the thenar muscle group. |
| Channel 3: | Electrodes 1 and 2 for stimulating the wrist extensor muscle group. |
| Channel 4: | Electrodes 3 and 4 for stimulating the wrist flexor muscle group. |

The sensors is 0 to 5 volts with a resolution of 256. The two input thresholds are set a one of 256 levels.

The input channels are associated with the following sensors:

| | |
|---|---|
| channel 1: | The Accelerometer for detecting the tilt angle of the palm during wrist extension. |
| Channel 2: | The gyroscope for detecting the lateral rotation of the wrist by measuring the angular velocity. |

A pressure sensor is also included on the orthotic. It provides an on/off switch to trigger the Portable Stimulator Unit for mode 2 stimulation (described below). It is very thin for the pressure sensor, therefore the sensor can attached on the surface of the sensor cluster.

The functional electrical stimulation system has 3 control modes selectable at the portable simulation unit.

Mode 1 is a simple exercise control. The patient chooses a muscle group to exercise and the simulation unit repeatedly stimulates that muscle group until the patient exits the mode.

Mode 2 is a manual mode in which the patient manually initiates a single stimulation of a selected muscle group. The pressure sensor on the orthotic can be used to initiate the stimulation.

Mode 3 is an automated stimulation mode in which the portable stimulation unit monitors feedback from the sensors and initiates a stimulation if the inputs exceed the input thresholds. The sensors capture the patients intention from their voluntary residual movement on the affected upper limb. This mode can initiate two different types of movement and then generate two different stimulation patterns controlling two different hand postures: hand opening for spastic hand, and Lateral Grasp for holding a pen.

Figure 10:
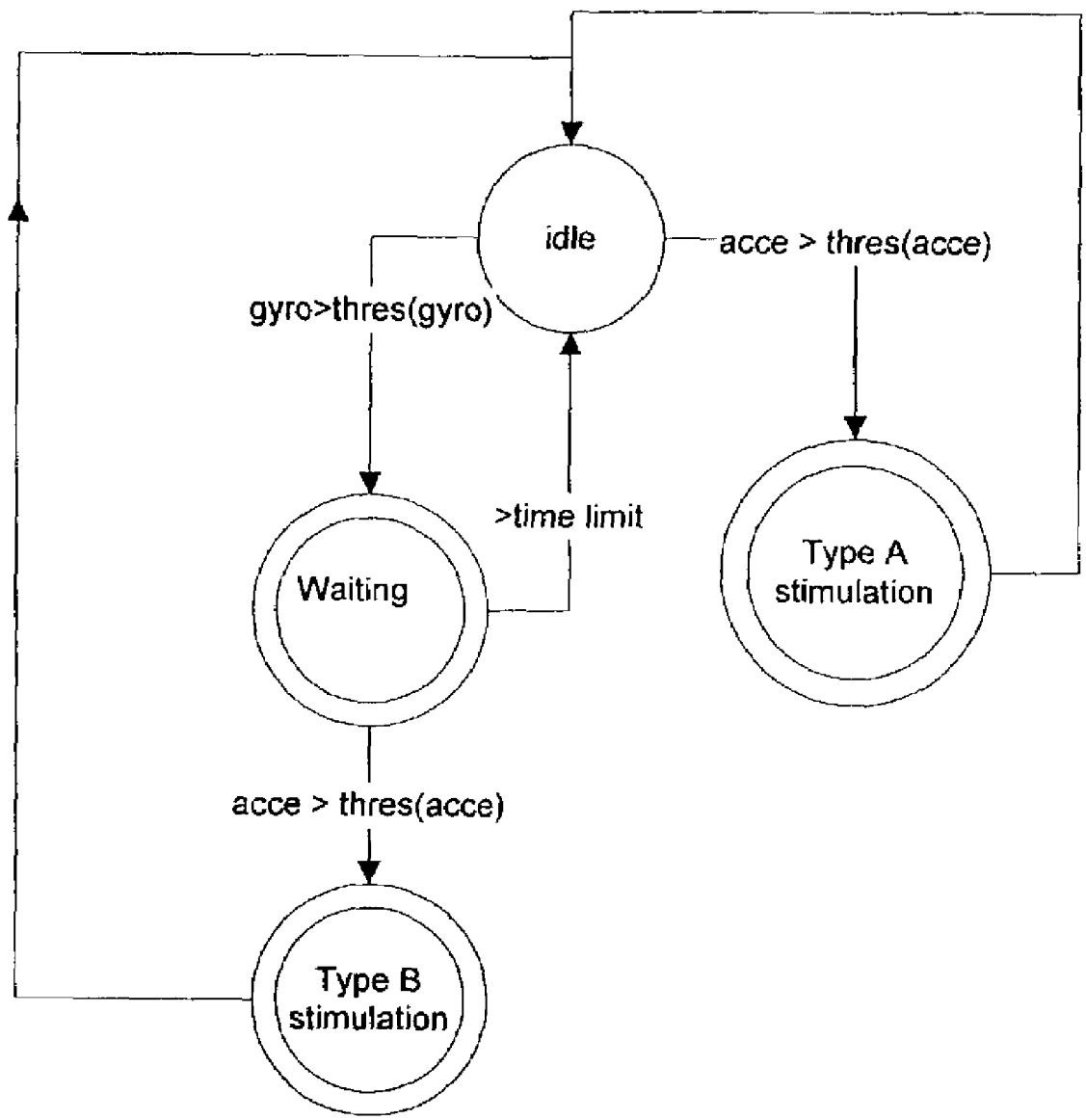
FIG. 10 is a flow diagram of a control strategy of the FES system.

Referring to FIG. 10, if the accelerometer sensor signal on input channel 1 is above threshold 1 the system enters stimulation A control. The microprocessor waits for the period set in the "Delay Time" parameter and then activates both Channel 1 (Electrodes 6) and Channel 3 (Electrodes 1 and 2) output signals to stimulate the respective muscles/muscle groups. The channels are closed again after the period of time set in the "Duration Time" parameter. The microprocessor enters an Idle stage for the period of time set in the "Reset Time" parameter. This is to prevent the functional electrical stimulation system immediately repeating the stimulation if the input 1 signal is still above the threshold 1 value.

A stimulation B is triggered by lateral wrist rotation followed by wrist extension. If the gyroscope sensor input on channel 2 is above the input 2 threshold the microprocessor will enter the Waiting stage. If the accelerometer sensor signal on input channel 1 does not go above threshold 1 within the "Reset time", then the microprocessor will return back to Idle stage. If the accelerometer sensor signal on input channel 1 goes above threshold 1 within the "Reset Time" the microprocessor enters Stimulation B control. The microprocessor waits for the period set in the "Delay Time" parameter and then activates both Channel 2 (Electrodes 5) and Channel 3 (Electrodes 1 and 2). The channels are closed again after the period of time set in the "Duration Time" parameter. The microprocessor enters an Idle stage for the period of time set in the "Reset Time" parameter. This is to prevent the functional electrical stimulation system immediately repeating the stimulation if the input signals is still above the threshold values.

The functional electrical stimulation system triggers the stimulation pattern through the sensors to capture the patients intention from their voluntary residual movement on the affected upper limb. There are lots of patients after stoke who still have partially voluntary movement on hand and wrist. By encouraging their hand movement, the patients can gradually re-learn the function movement. The present invention could help the user to motor-relearn the functional movements.

Where in the foregoing description reference has been made to integers or elements having known equivalents then such are included as if individually set forth herein.

Embodiments of the invention have been described, however it is understood that variations, improvements or modifications can take place without departure from the spirit of the invention or scope of the appended claims.

What is claim is:

1. An electrical stimulation device for aiding movement of a partials paralysed body part, comprising:
   an orthotic for wearing on a body part of a person,
   a first sensor on the orthotic for detecting a first movement of the body part and if a first movement of the body part is detected producing a sensor signal,
   a second sensor on the orthotic for detecting a second movement of the body part and if a second movement of the body part is detected producing a second sensor signal.
   a plurality of electrodes on the orthotic for contacting the skin surface over muscles used to move the body part, the electrodes separated into two groups,and a controller in electrical communication with the sensors and electrodes for receiving the first sensor signal and comparing it to a first threshold value, receiving the second sensor signal and comparing it to a second threshold value, and generating an electrical output from a first group of electrodes if the first sensor signal exceeds the first threshold value, or generating the an electrical output from a second group of electrodes if the first sensor signal exceeds the first threshold value and the second sensor signal exceeds the second threshold value, wherein the body part is an upper limb the first movement is extension of the wrist the second movement is rotation of the wrist and the muscles are thumb abductor, thenar, wrist extensor, and wrist flexor muscles.

2. The device of claim 1 wherein the first sensor is an accelerometer and the first movement is extension of the wrist, and second sensor is a gyroscope and the second movement is rotation of the wrist.

3. The device of claim 1 wherein the orthotic includes a first elongate member for locating on a anterior portion of a forearm of the person, a dorsal strap extending across a posterior portion of the forearm, a second elongate member disposed on the dorsal strap of locating against the posterior portion of the forearm, and a hand member for locating about a wrist and palm of the person, the wrist member being flexibly engaged with the first elongate member for allowing movement of the wrist.

4. The device of claim 1 including a docking station for connecting the electrodes and sensors to a computer, the docking station including a first processor for measuring values of the sensor signals and the electrical output and communicating said values to the computer, and a second processor for generating electrical outputs on the electrodes in response to communications from the computer.

5. The device of claim 1 wherein the controller is connectable to the computer for uploading parameters including the first and second threshold values from the computer to the controller.

6. The device of claim 1 wherein the first group of electrodes are located on the skin surface over the thumb abductor and wrist extensor muscles, and the second group of electrodes are located on the skin surface over the Thenar and wrist extensor muscles.

* * * * *